United States Patent [19]

Shibuya et al.

[11] 4,172,197

[45] Oct. 23, 1979

[54] CEPHALOSPORIN DERIVATIVES AND PROCESS FOR PREPARING THE SAME

[75] Inventors: Chisei Shibuya; Hirataka Itoh, both of Fuji; Yutaka Usubuchi, Yokohama; Mitsuaki Akamine, Fuji, all of Japan

[73] Assignee: Asahi Kasei Kogyo Kabushiki Kaisha, Osaka, Japan

[21] Appl. No.: 644,241

[22] Filed: Dec. 24, 1975

[30] Foreign Application Priority Data

Dec. 28, 1974 [JP] Japan ................................ 49-149180
Jun. 11, 1975 [JP] Japan ................................ 50-69589
Jul. 15, 1975 [JP] Japan ................................ 50-85763

[51] Int. Cl.$^2$ ................. C07D 501/34; C07D 501/36; C07D 501/46
[52] U.S. Cl. ........................................ 544/27; 544/15; 544/22; 544/24; 544/25; 544/26; 544/28; 544/29; 544/30; 424/246
[58] Field of Search ............... 260/243 C; 544/15, 22, 544/24, 25, 26, 27, 28, 29, 30; 424/246

[56] References Cited

U.S. PATENT DOCUMENTS

| 3,382,238 | 5/1968 | Dolfini et al. | 260/243 C |
|---|---|---|---|
| 3,865,819 | 2/1975 | DeMarinis et al. | 260/243 C |
| 3,880,848 | 4/1975 | DeMarinis et al. | 260/243 C |
| 3,904,606 | 9/1975 | Williams | 260/239.1 |
| 3,912,726 | 10/1975 | Diassi et al. | 260/243 C |
| 4,045,438 | 8/1977 | Haviv et al. | 544/27 |
| 4,093,723 | 6/1978 | Berges | 544/27 |
| 4,096,256 | 6/1978 | Berges | 544/27 |
| 4,118,491 | 10/1978 | Berges | 544/27 |

OTHER PUBLICATIONS

The Merck Index, 8th Ed., Merck & Co., Rahway, N.J. (1968), pp. 791 and 1712.

*Primary Examiner*—David Wheeler
*Attorney, Agent, or Firm*—Cushman, Darby & Cushman

[57] ABSTRACT

Novel cephalosporin derivatives having a higher microbial activity across a broad antimicrobial spectrum. They are useful for treatment of infections caused by Gram-positive bacteria and Gram-negative bacteria. Such cephalosporin derivatives are prepared by a relatively simple method.

86 Claims, No Drawings

CEPHALOSPORIN DERIVATIVES AND PROCESS FOR PREPARING THE SAME

This invention relates to novel cephalosporin derivatives having an antimicrobial activity across a broad antimicrobial spectrum and salts thereof and a process for preparing the same.

It is known that cephalosporin derivatives are compounds having an antimicrobial activity. However, in order to obtain sufficient antimicrobial effects, it is necessary to use these known cephalosporin derivatives in large quantities.

It is therefore a primary object of this invention to provide cephalosporin derivatives having a higher microbial activity.

Another object of this invention is to provide a process for preparing these cephalosporin derivatives having a higher antimicrobial activity.

As a result of our research works made with a view to developing novel cephalosporin derivatives having a higher microbial activity across a broad antimicrobial spectrum, we have found that compounds represented by the following general formula (I), in which the sulfinyl group is of the R form, have a higher antimicrobial activity:

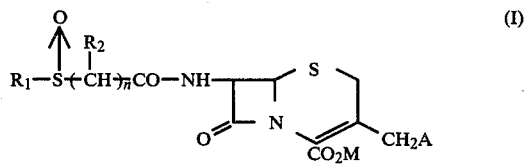

(I)

wherein $R_1$ stands for a heterocyclic group to a heterocyclic group-substituted lower alkyl group, an aryl group or an aralkyl group, $R_2$ stands for a hydrogen atom or a lower alkyl group, A stands for a hydrogen atom, a hydroxy group, a lower alkanoyloxy group, a basic nitrogen-containing group, a quaternary ammonium group, an N-substituted or N-unsubstituted carbamoyloxy group, an aroyloxy group, an aralkanoyloxy group, a lower alkoxy group, a mercapto group, a lower alkyl mercapto group, an aryl mercapto group, a heterocyclic group-substituted mercapto group or an azido group, M stands for a hydrogen atom, a lower alkyl group, an aralkyl group, a tri-substituted silyl group, a group —$CH_2OCOR_3$ in which $R_3$ is a lower alkyl, aryl or aralkyl group, a phenacyl group, a pharmacologically acceptable non-toxic cation, an anionic charge or a monovalent carbon-oxygen bond when taken together with A, and n is 1, 2 or 3, wherein said R form is defined to indicate an optical isomer having stereochemically the same structure as that of an optical isomer having a positive specific rotation $[\alpha]_D$ in ethanol between the specific rotations of two sulfinyl group stereoisomers of a compound represented by the following general formula (II):

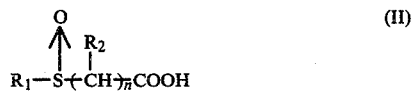

(II)

wherein $R_1$, $R_2$ and n are as defined above.

The compound represented by the above general formula (II) is asymmetric in the sulfinyl group and includes two optical isomers. Accordingly, cephalosporins derived from this compound include two kinds of optical isomers in the sulfinyl group. It has been found that cephalosporins derived from an optical isomer having a positive specific rotation $[\alpha]_D$ in ethanol between the specific rotations of two isomers of the compound represented by the above general formula (II) and cephalosporins derived from a mixture containing an optical isomer of the compound of the above formula (II) having a positive specific rotation $[\alpha]_D$ in ethanol have a higher antimicrobial activity than corresponding cephalosporins derived from the other optical isomer of the compound of the above general formula (II) having a negative specific rotation $[\alpha]_D$ in ethanol.

Definitions of respective symbols in the above general formula (I) will now be described.

In the present invention, by the heterocyclic group is meant a heterocyclic ring residue containing at least one hetero-atom selected from nitrogen, oxygen and sulfur in a monocyclic or bicyclic structure. Accordingly, the heterocyclic group may further contain a substituent or substituents. As specific examples of the heterocyclic group, there can be mentioned a thienyl group, a furyl group, a pyridyl group, an imidazolyl group, an oxazolyl group, oxadiazolyl groups such as 1,2,3-oxadiazolyl, 1,2,4-oxadiazolyl, 1,2,5-oxadiazolyl and 1,3,4-oxadiazolyl groups, a thiazolyl group, thiadiazolyl groups such as 1,2,3-thiadiazolyl, 1,2,5-thiadiazolyl and 1,3,4-thiadiazolyl groups, tetrazolyl groups such as 1-H-tetrazolyl and 2-H-tetrazolyl groups, a benzothiazolyl group, an isoxazolyl group, a benzozadinyl group, a benzoxazinyl group, a pyridazinyl group, etc. These heterocyclic groups may be substituted or unsubstituted. In pyridyl and pyridazinyl groups, one of the nitrogen atoms may be in the form of an oxide. Further, in the pyridyl group, the nitrogen atom may be quaternized by a lower alkyl group.

As the substituent for the heterocyclic group, there can be mentioned lower alkyl groups, lower alkenyl groups, halogen atoms, aryl groups, aralkyl groups and groups containing sulfur, nitrogen or oxygen. As specific examples, there can be mentioned a hydroxyl group, a cyano group, a carboxyl group, a nitro group, an amino group, a monoalkylamino group, a dialkylamino group, a dialkylaminomethyl group, a lower alkoxy group, a lower alkoxymethyl group, a lower alkylthio group, a sulfonyl group, a mercapto group and a pyridyl group.

By the lower alkyl group is meant a linear or branched alkyl group having 1 to 8 carbon atoms. As specific examples, there can be mentioned methyl, ethyl, propyl, isopropyl, butyl, isobutyl, t-butyl and amyl groups. The lower alkoxy and lower alkyl mercapto groups include corresponding alkoxy and alkylmercapto groups.

By the aralkyl group is meant a group consisting of a lower alkyl group such as mentioned above and an aryl group bonded to said lower alkyl group. By the aryl group is meant a phenyl group or a substituted phenyl group having 1 to 3 substituents, preferably 1 substituent. As the substituent, there can be mentioned, for example, halogen atoms, lower alkoxy groups (the lower alkyl group being as defined above), a hydroxyl group, a cyano group, a carboxyl group, an amino group and di-(lower alkyl)-amino group.

As specific examples of the aryl group, there can be mentioned a phenyl group, o-, m- and p-chlorophenyl group, o-, m- and p-bromophenyl groups, a 3,4- dichlorophenyl group, a 3,5-dibromophenyl group, o-, m- and p-tolyl groups, a p-methoxyphenyl group, a 3,4,5-trimethoxyphenyl group, a p-hydroxyphenyl group, an o-carboxyphenyl group and a naphthyl group. As specific examples of the aralkyl group including an aryl group such as mentioned above, there can be mentioned a benzyl group, o-, m- and p-bromobenzyl groups, o-, m- and p-methoxybenzyl group, a phenethyl group, a p-chlorophenethyl group, a 3,5-diethylbenzyl group and a 3,4,5-trichlorobenzyl group.

Lower alkanoyloxy, aroyloxy and aralkanoyloxy groups indicate groups containing an acyl residue of an acid ester. More specifically, the lower alkanoyl moiety of the lower alkanoyloxy group is an acyl residue of a lower fatty acid containing a lower alkyl group such as mentioned above. As specific examples of the lower alkanoyloxy group, there can be mentioned an acetoxy group, a propionyloxy group and a butyryloxy group. The aroyloxy group includes similar groups derived from aryl groups such as mentioned above, and the aralkanoyloxy group includes similar groups consisting of an alkanoyloxy group such as mentioned above and bonded thereto, an aryl group such as mentioned above.

The basic nitrogen-containing group includes amine residues such as residues of alkylamines, e.g., methylamine, ethylamine, dimethylamine and triethylamine, and the quaternary ammonium group includes residues of N,N'-dibenzyl pyridinium, pyridinium, 1-quinolinium and 1-picolinium.

As the substituted or unsubstituted carbamoyloxy group, there can be mentioned, for example, carbamoyloxy, thiocarbamoyloxy, N-lower alkyl-carbamoyloxy, N-lower alkyl-thiocarbamoyloxy, N,N-di-(lower alkyl)-carbamoyloxy and N,N-di-(lower alkyl)-thiocarbamoyloxy groups.

Further, as pointed out hereinbefore, A and M may be bonded together to form a monovalent carbon-oxygen bond in the lactone ring.

As the non-toxic cation as M, there can be mentioned, for example, ions of metals such as aluminum, alkali metals, e.g., sodium and potassium, and alkaline earth metals, e.g., calcium and magnesium, and ions of amine salts, for example, generally known amine salts, such as salts of benzylamine, N,N-dibenzylethylene diamine, methylamine, triethylamine, procaine and N-ethylpiperidine.

By the trisubstituted silyl group is meant a silyl group having three substituents selected from lower alkyl groups, aryl groups and aralkyl groups such as mentioned above.

Specific examples of the portion

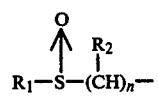

in the intended compound of the present invention are as follows:

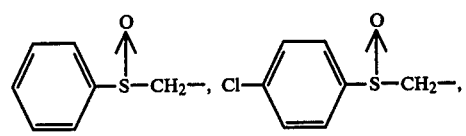

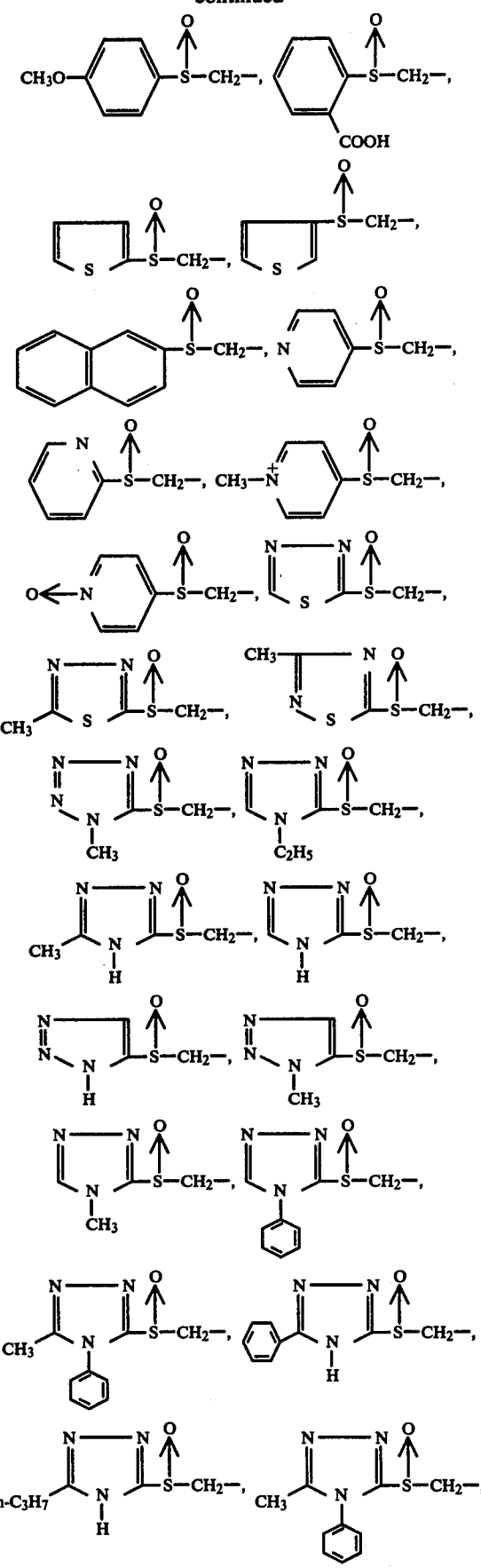

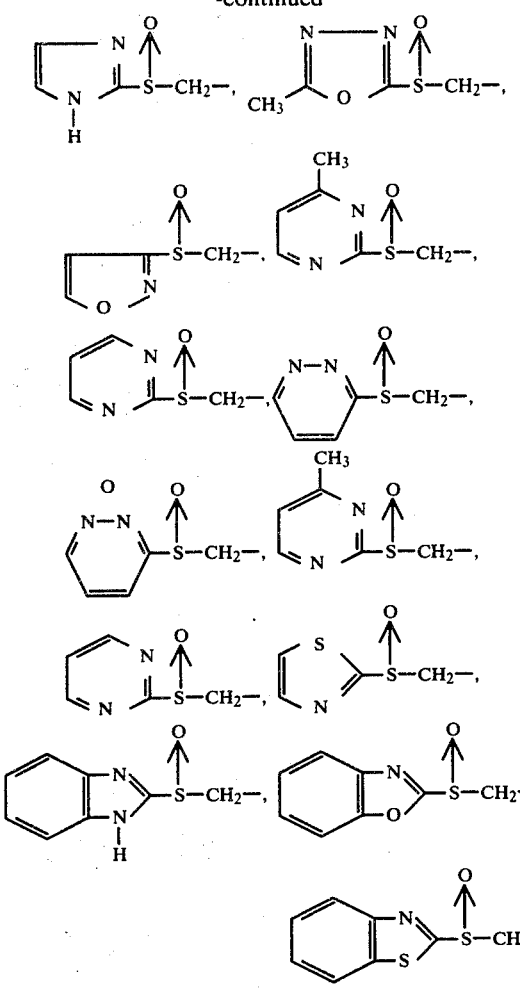
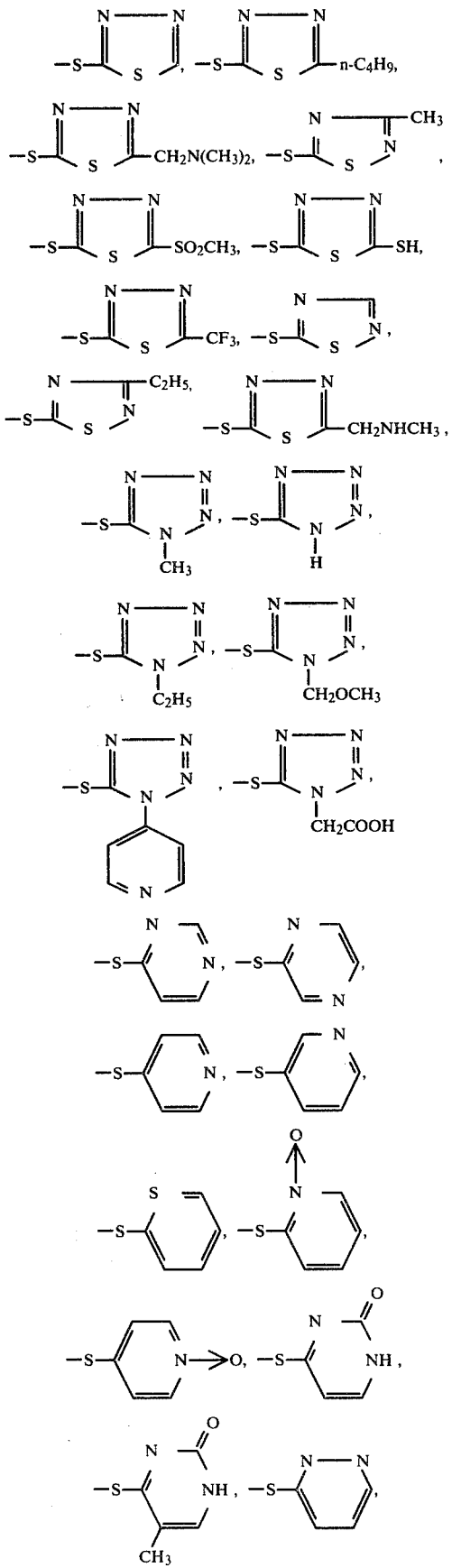
Specific examples of A in the above general formula (I) are as follows:
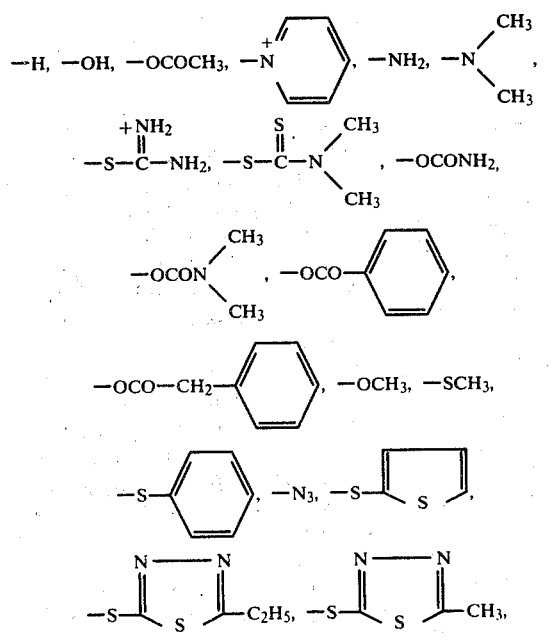

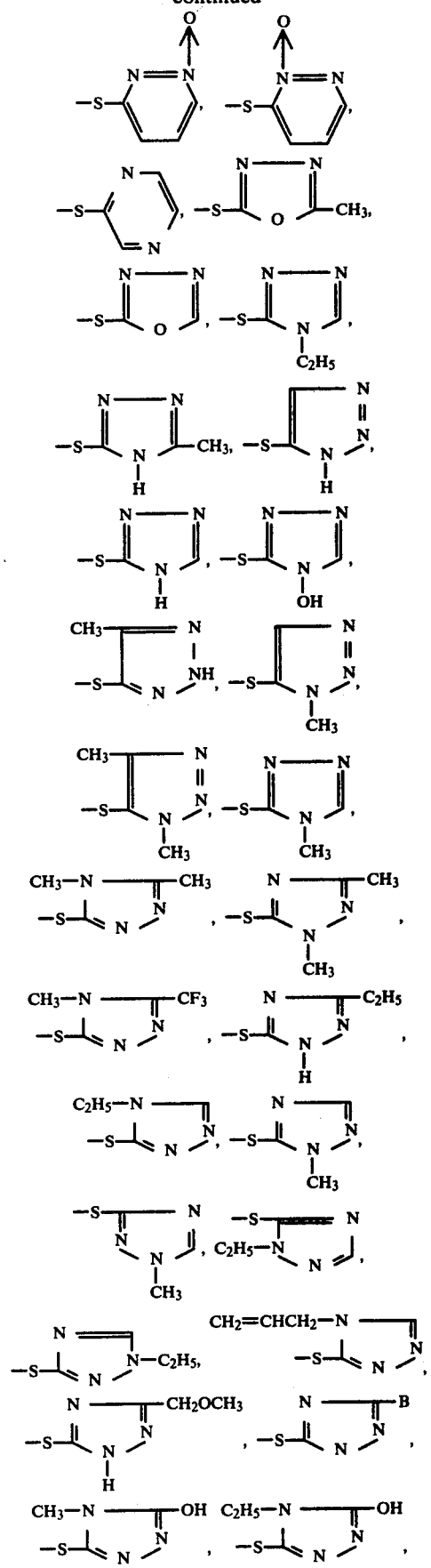
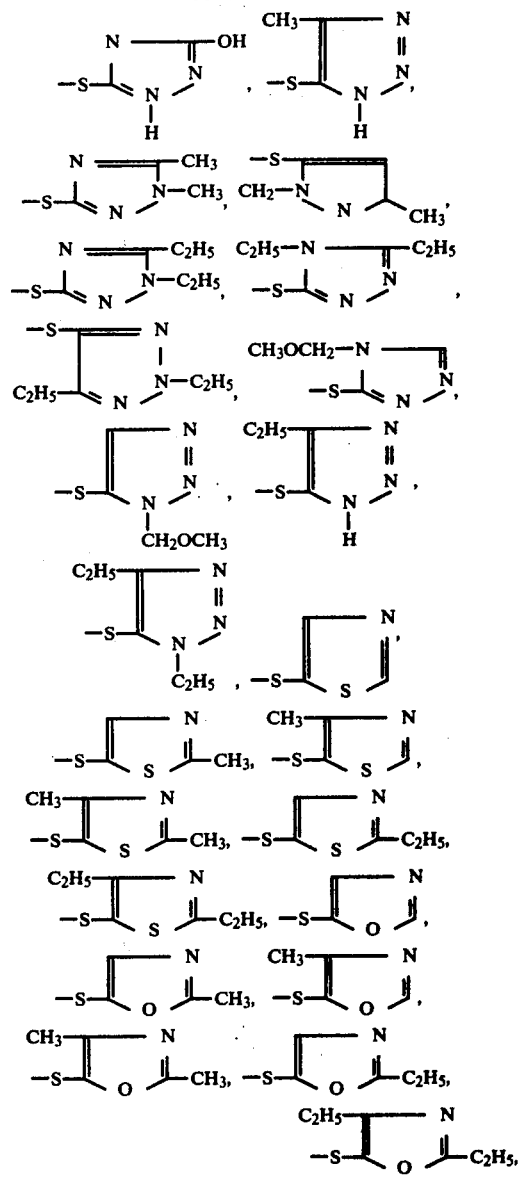

Especially preferred examples of the group $R_1$ include thienyl, pyridyl, thiadiazolyl, tetrazolyl, imidazolyl, triazolyl, pyrimidyl, isoxazolyl, phenyl, p-chlorophenyl, tolyl and p-methoxyphenyl groups which may be unsubstituted or substituted by lower alkyl or aryl groups. More preferred examples include 2-thienyl, 3-thienyl, 2-pyridyl, 4-pyridyl, 5-methyl-1,3,4-thiadiazol-2-yl, 1,3,4-thiadiazol-2-yl, 2-imidazolyl, 3-isoxazolyl, 1-methyl-1H-tetrazol-5-yl, 1,2,4-triazol-3-yl, 2-pyrimidyl and phenyl groups.

Especially preferred examples of A include a hydrogen atom, a hydroxyl group and lower alkanoyloxy, pyridinium, tetrazolylthio, thiazolylthio, triazolylthio, methoxy and methylthio groups. More preferred examples include a hydrogen atom and acetoxy, 1-methyl-1H-tetrazol-5-ylthio and 5-methyl-1,3,4-thiadiazol-2-ylthio groups.

Compounds of the above general formula (I) in which $R_2$ is a hydrogen atom and n is 1 have a highest antimicrobial activity.

Compounds of the present invention can be prepared by the following methods.

Method (A)

A compound represented by the following formula (III):

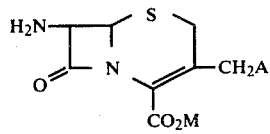

wherein A and M are as defined above, or its reactive derivative is reacted with a compound of the R form represented by the above general formula (II) or its activated forms.

The carboxylic acid of the R form represented by the above general formula (II) is a carboxylic acid formed by bonding a group —COOH to the portion of the R form

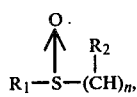

in the intended compound of the present invention. In other words, the carboxylic acid of the above formula (II) has a positive specific rotation $[\alpha]_D$ in ethanol.

As the reactive derivative of the compound of the formula (III), there can be mentioned a silyl ester and an amine salt.

As the activated forms of the carboxylic acid of the formula (II), there can be mentioned, for example, acid chlorides, acid anhydrides, amides, azides, active esters and salts formed with an alkali metal, an alkaline earth metal, ammonia or an organic base.

The reaction between the compound of the formula (II) and the compound of the formula (III) is carried out in a suitable solvent such as acetone, dioxane, tetrahydrofuran, acetonitrile, chloroform or methylene chloride, if desired in the presence of a base such as sodium bicarbonate or potassium bicarbonate, at room temperature or under cooling.

When the compound of the above formula (II) is reacted in the form of a free acid or salt, it is preferred that the reaction be carried out in the presence of an acid binder such as dicyclohexyl carbodiimide, diphenyl phosphoric azide, diethyl phosphoric cyanide, hexachlorotriphosphotriazine or triazine trichloride.

Method (B)

When a substituent A is a nucleophilic group, the intended compound is prepared by condensing 7-aminocephalosporanic acid with a carboxylic acid of the above formula (II) and substituting the acetoxy group of the resulting cephalosporin with a nucleophilic group.

Method (C)

A compound of the above formula (III) is acylated with a carboxylic acid of the above formula (II) or its activated form with the aid of an acylating enzyme, whereby a cephalosporin of the formula (I) is formed.

Method (D)

When the starting carboxylic acid of the R form represented by the above formula (II) contains an equal or minor amount of an isomer having in the sulfinyl group a stereostructure reverse to that of the R form (having a negative specific rotation $[\alpha]_D$ in ethanol), the resulting cephalosporin is subjected to chromatography, for example, reversed phase partition chromatography, or to recrystallization treatment, whereby the intended compound of the R form is recovered.

In general, the reaction temperature in the process of this invention is not critical but the reaction is preferably conducted under cooling, for example at about −20° C. to 0° C. or at room temperature. The reaction period also is not critical and it may be varied, for example, from several minutes to several hours, depending upon the kind and type of starting material and reaction solvent employed, the reaction temperature applied and other factors.

Compounds of the present invention represented by the above general formula (I) have a high antimicrobial activity to Gram-positive bacteria and Gram-negative bacteria in animals and men. Accordingly, they are effective for remedy of diseases infected by these bacteria, such as air-passage diseases, e.g., bronchitis, pneumonia and pleurisy, diseases of liver, gall and abdomen, e.g., cholecystitis and peritonitis, diseases of blood and cardiac vessels, e.g., septicemia, urinary passage diseases, e.g., pyelitis, nephritis and cystitis, and otorhinolaryngological diseases, e.g., tympanitis and parotitis.

The present invention, in a further aspect, is directed to pharmaceutical compositions incorporating a compound of the formula (I) hereof as an essential active component in admixture with a pharmaceutically acceptable non-toxic carrier.

The compounds of the present invention can be absorbed effectively in living bodies by oral administration or parenteral administration. In the latter case, the active compounds are in suitable solvents such as sterilized water, physiological saline solution, glucose solution and ordinary injection liquids and electrolytic solutions.

The amount to be administered, that is, the dosage of the active cephalosporin compound (I) should be determined by skilled physicians taking consideration of the ages and weight of patients, kinds and severities of disorders and other factors, but there is usually employed the total daily dosage for adults of about 250 to 1,000 mg., preferably in multiple doses such as three or more times a day, while larger total daily dosages may be effectively employed in some cases.

The present invention will now be described in detail by reference to the following Examples that by no means limit the scope of the present invention.

REFERENTIAL EXAMPLE 1

11.6 g of 2-mercaptothiophene and 10.4 g of monochloroacetic acid were refluxed for 3 hours with 8.8 g of sodium hydroxide and 100 ml of water, and the pH of the reaction mixture was adjusted to 2.0 by addition of hydrochloric acid to precipitate an oily substance. The precipitate was extracted with ethyl acetate, dried with anhydrous sodium sulfate and concentrated to obtain 12.1 g of a light yellow crystal. Results of the NMR spectrum analysis (CDCl$_3$) of the product were as follows:

δ3.5 (singlet, 2H), δ6.9–7.4 (multiplet, 3H), δ11.6 (singlet, 1H)

REFERENTIAL EXAMPLE 2

8.7 g of 2-thienylthioacetic acid was dissolved in 30 ml of acetic acid and 6.8 ml of 30% aqueous hydrogen peroxide was added under ice cooling and agitation. The mixture was agitated at room temperature for 5 hours. Acetic acid was removed from the reaction mixture under reduced pressure, and the residue was recrystallized from ethyl acetate to obtain 5.3 g of 2-thienylsulfinyl acetic acid having a melting point of 114° to 116° C. Results of the NMR spectrum analysis (DMSO-$d_6$) of this compound were as follows:

δ4.1 (singlet, 2H), δ7.15 (multiplet, 1H), δ7.55 (triplet, 1H), δ7.9 (doublet, 1H) Elementary analysis values of the product as $C_6H_6S_2O_3$ were as follows:
Calculated: C=37.88%, H=3.18%, S=33.71%
Found: C=37.76%, H=3.31%, S=33.48%

REFERENTIAL EXAMPLE 3

1.00 g of 2-thienylsulfinylacetic acid and 2.57 g of brucine were dissolved in 25 ml of ethanol, and the solution was concentrated and dried to the solid. The residual powder was washed with 35 ml of hot benzene, and the insoluble solids were recrystallized from 20 ml of ethanol and 1.50 g of the obtained crystal was treated with hydrochloric acid and extracted with ethyl acetate. The organic layer was concentrated and crystallized from ethyl acetate to obtain 0.35 g of optically active 2-thienylsulfinylacetic acid. The specific rotation $[\alpha]_D^{22°}$ of the so obtained compound in ethanol was +11.0° at C=1.0 (the concentration being 1.0% in ethanol).

EXAMPLE 1

0.38 g of 2-thienylsulfinylacetic acid ($[\alpha]_D^{22°}$:+11.0°, C=1.00, ethanol) obtained according to the method described in Referential Example 3 was dissolved in 8 ml of dry acetone, and 0.28 ml of triethylamine and 3 drops of N,N-dimethylbenzylamine were added to the solution. The mixture was agitated and cooled to −10° C., and 0.24 g of pivaloyl chloride was added thereto. Then, the mixture was agitated at −10° C. for 30 minutes, and a liquid mixture of 0.54 g of 7-aminocephalosporanic acid, 0.28 g of triethylamine, 3 ml of acetone and 3 ml of water was added at a stroke to the above mixture under violent agitation at the above temperature. Then, the mixture was agitated for 30 minutes at −10° C., for 1 hour at 0° C. and for another 1 hour at room temperature. The liquid reaction mixture was concentrated at a temperature lower than 40° C. and washed with ethyl acetate. The pH was adjusted to 3 by 2 N hydrochloric acid and the mixture was extracted with ethyl acetate. The organic layer was concentrated under reduced pressure and dried under reduced pressure to obtain 0.43 g of a crude crystal containing 7-(2-thienylsulfinylacetamido)cephalosporanic acid of the R modification which was optically active in the sulfoxide. The crude crystal was subjected to column chromatography using Sephadex Lh-20 (manufactured by Pharmacia Fine Chemicals AB) and methanol as the solvent, and the pure product was fractionally recovered.

NMR Spectrum (DMSO-$d_6$), δ ppm:
2.0 (singlet, 3H), 3.6 (quadruplet, 2H), 4.1 (quadruplet, 2H), 4.8 (quadruplet, 2H), 5.1 (doublet, 1H), 5.7 (quadruplet, 1H), 5.1 (doublet, 1H), 5.7 (quadruplet, 1H), 7.2 (triplet, 1H), 7.6 (doublet, 1H), 8.0 (doublet, 1H), 9.2 (doublet, 1H)

Elementary Analysis Values as $C_{16}H_{16}N_2O_7S_3.\frac{1}{2}H_2O$:
Calculated: C=42.3%, H=3.78%, N=6.18%, S=21.21% Found: C=42.52%, H=4.15%, N=5.78%, S=20.85%

The minimum inhibitory concentrations (μ/ml) (MIC) of the so obtained compound to various Gram-positive bacteria and Gram-negative bacteria are shown in Table 1. For comparison, MIC data of a cephalosporin derivative formed from 2-thienylsulfinylacetic acid having $[\alpha]_D^{20°}$ of −9.2° according to the method described in Comparative Example given hereinafter.

Table 1

| Bacterium | 7-(2-Thienyl-sulfinyl-acetamido) cephalosporanic acid | 7-(2-Thienyl-sulfinylacetamido) cephalosporanic acid |
|---|---|---|
| $[\alpha]_D^{22°}$ in ethanol of starting 2-thienylsulfinyl-acetic acid | +11.0 | −9.2 |
| Staphylococcus aureus, ATCC 6538 P | 0.8 | 1.6 |
| Staphylococcus aureus, ATCC MS 27 | 1.6 | 6.3 |
| Escherichia coli, NIHJ | 1.6 | 6.3 |
| Escherichia coli, W 3630 | 12.5 | 50 |
| Salmonella enteritidis gaertner | 1.6 | 12.5 |
| Klebsiella pneumoniae, ATCC 10031 | 0.8 | 6.3 |
| Shigella sonnei E 33 | 3.1 | 25 |
| Proteus rettgeri, ACR | 100 | 100 |
| Pseudomonas aeruginosa | 100 | 100 |

Even when the above crude crystal was used, excellent inhibiting effects were similarly confirmed.

COMPARATIVE EXAMPLE 0.38 G of 2-thienylsulfinylacetic acid ($[\alpha]_D^{22°}$:−9.2°, C=1.00, ethanol) was dissolved in 8 ml of dry acetone, and 0.28 ml of triethylamine and 3 drops of N,N-dimethylbenzylamine were added to the solution and the mixture was agitated. The resulting solution was cooled to −10° C. and 0.24 g of pivaryl chloride was added thereto under agitation. The mixture was agitated at −10° C. for 30 minutes, and a liquid mixture of 0.54 g of 7-aminocephalosporanic acid, 0.28 g of triethylamine, 3 ml of acetone and 3 ml of water was added at a stroke under violent agitation at the above temperature. The reaction mixture was agitated at −10° C. for 30 minutes, at 0° C. for 1 hour and at room temperature for another 1 hour. The liquid reaction mixture was concentrated at a temperature lower than 40° C. and the residue was dissolved in a 3% aqueous solution of sodium hydrogencarbonate and washed with ethyl acetate. The pH was adjusted to 3 by 2 N hydrochloric acid, and extraction was conducted with ethyl acetate. The organic layer was concentrated and dried under reduced pressure to obtain 0.38 g of a crude crystal of 7-(2-thienylsulfinylacetamido)cephalosporanic acid which was optically active in the sulfoxide. The NMR spectrum of the product was substantially in agreement with that of the compound obtained in Example 1.

EXAMPLE 2

150 g of a mixture of diastereomers of 7-(2-thienylsulfinylacetamido)cephalosporanic acid which was substantially optically inactive in the sulfoxide was separated by reverse phase chromatography using a nonpolar coating resin as a carrier and water-methanol as a solvent. The main components of the thus separated two fractions were found to be in agreement with two kinds of 7-(2-thienylsulfinylacetamido)cephalosporanic acid derived from 2-thienylsulfinylacetic acid optically active in the sulfoxide. The specific rotation $[\alpha]_D^{25°}$ of the fraction containing the compound of Example 1 in a major amount was +115.9° (C=0.80, chloroform).

EXAMPLE 3

300 mg of 7-(2-thienylsulfinylacetamido)cephalosporanic acid of the R form optically active in the sulfoxide, which was synthesized according to the method described in Example 1, 130 mg of sodium hydrogencarbonate and 140 mg of 2-mercapto-5-methyl-1,3,4-thiadiazole were heated and agitated at 60° C. for 5 hours in 6 ml of a phosphoric acid buffer solution having a pH of 6.5. Then, the pH of the reaction mixture was adjusted to 2.5 and the resulting precipitate was collected and dried to obtain 220 mg of a crude crystal of 7-(2-thienylsulfinylacetamido)-3-(5-methyl-1,3,4-thiadiazol-2-ylthiomethyl)-3-cephem-4-carboxylic acid optically active in the sulfoxide. The pure product was obtained by recrystallizing the crude crystal from water-acetone. The minimum inhibitory concentration (MIC) of the product was much superior to that of the product similarly derived from the compound obtained according to the method described in Comparative Example.

NMR Spectrum (DMSO-d$_6$), ppm:

2.7 (singlet, 3H), 3.7 (quadruplet, 2H), 4.1 (quadruplet, 2H), 4.5 (quadruplet, 2H), 5.1 (doublet, 1H), 5.7 (quadruplet, 1H), 7.2 (triplet, 1H), 7.6 (doublet, 1H), 8.0 (doublet, 1H), 9.2 (doublet, 1H)

EXAMPLE 4

154 mg of t-butyl 7-amino-3-(1-methyl-1H-tetrazol-5-ylthiomethyl)-3-cephem-4-carboxylate and 83 mg of dicyclohexylcarbodiimide were dissolved in 5 ml of benzene, and 76 mg of 2-thienylsulfinylacetic acid ($[\alpha]_D^{22°}$:+11.0°, C=1.00, ethanol) was added to the solution. This liquid reaction mixture was agitated at 25° C. for 2 hours. The mixture was filtered, made adsorbed on 2 g of silica gel and subjected to chromatography using benzene-ethyl acetate (50:50) on 20 g of silica gel to obtain 145 mg of t-butyl 7-(2-thienylsulfinylacetamido)-3-(1-methyl-1H-tetrazol-5-ylthiomethyl)-3-cephem-4-carboxylate. The so obtained ester was dissolved in 1 ml of trifluoroacetic acid, and the solution was agitated at 25° C. for 5 minutes. Then, the solution was added dropwise to 70 ml of ether. The resulting precipitate was collected and dissolved in 5% aqueous sodium bicarbonate solution to form 100 ml of a solution. Then, the solution was extracted with ethyl acetate, and the pH of the aqueous layer was adjusted to 2.0 and the aqueous layer was further extracted with ethyl acetate. The organic layer was dried and concentrated until the volume was reduced to 5 ml. The resulting residue was mixed with a 30% solution of sodium 2-ethylhexanoate in propanol, and ether was added to the mixture. The precipitated salt was collected, recrystallized from methanolether and dried under reduced pressure to obtain 51 mg of sodium 7-(2-thienylsulfinylacetamido)-3-(1-methyl-1H-tetrazol-5-ylthiomethyl)-3-cephem-4-carboxylate of the R form optically active in the sulfoxide. The NMR spectrum was found to be in agreement with that of the intended product.

The bacterium-inhibiting activity of the so obtained compound was much superior to that of the product derived in the same manner by using 2-thienylsulfinylacetic acid having $[\alpha]_D^{22°}$ of −9.2° as the starting compound.

EXAMPLE 5

7-Amino-3-heterocyclic-thiomethyl-3-cephem-4-carboxylic acids or t-butyl esters thereof were reacted with 2-thienylsulfinylacetic acid ($[\alpha]_D^{22°}$:+11.0°, C=1.00, ethanol) according to the method described in Example 1 or Example 4 to obtain the following corresponding 7-(2-thienylsulfinyl-acetamido)-3-heterocyclic-thiomethyl-3-cephem-4-carboxylic acids or sodium salts thereof, each being optically active in the sulfoxide and being excellent in the bacterium-inhibiting effect.

7-(2-Thienylsulfinylacetamido)-3-(2-pyridylthiomethyl)-3-cephem-4-carboxylic acid, 7-(2-thienylsulfinylacetamido)-3-(4-pyridylthiomethyl)-3-cephem-4-carboxylic acid, 7-(2-thienylsulfinylacetamido)-3-(1-oxo-4-pyridylthiomethyl)-3-cephem-4-carboxylic acid, 7-(2-thienylsulfinylacetamido)-3-(4-pyrimidylthiomethyl)-3-cephem-4-carboxylic acid, 7-(2-thienylsulfinylacetamido)-3-(2-oxo-4-pyrimidylthiomethyl)-3-cephem-4-carboxylic acid, 7-(2-thienylsulfinylacetamido)-3-(2-oxo-5-methyl-4-pyrimidylthiomethyl)-3-cephem-4-carboxylic acid, 7-(2-thienylsulfinylacetamido)-3-(3-pyridazinylthiomethyl)-3-cephem-4-carboxylic acid, 7-(2-thienylsulfinylacetamido)-3-(1-oxo-3-pyridazinylthiomethyl)-3-cephem-4-carboxylic acid, 7-(2-thienylsulfinylacetamido)-3-(2-oxo-3-pyridazinylthiomethyl)-3-cephem-4-carboxylic acid, 7-(2-thienylsulfinylacetamido)-3-(2-thienylthiomethyl)-3-cephem-4-carboxylic acid, 7-(2-thienylsulfinylacetamido)-3-(4-methyl-1,2,4-triazol-3-ylthiomethyl)-3-cephem-4-carboxylic acid, 7-(2-thienylsulfinylacetamido)-3-(5-methyl-1,2,4-triazol-3-ylthiomethyl)-3-cephem-4-carboxylic acid, 7-(2-thienylsulfinylacetamido)-3-(1-methyl-1,2,4-triazol-5-ylthiomethyl)-3-cephem-4-carboxylic acid, 7-(2-thienylsulfinylacetamido)-3-(1-methyl-1,2,4-triazol-3-ylthiomethyl)-3-cephem-4-carboxylic acid, 7-(2-thienylsulfinylacetamido)-3-(1,5-dimethyl-1,2,4-triazol-3-ylthiomethyl)-3-cephem-4-carboxylic acid, 7-(2-thienylsulfinylacetamido)-3-(1,3-dimethyl-1,2,4-triazol-5-ylthiomethyl)-3-cephem-4-carboxylic acid, 7-(2-thienylsulfinylacetamido)-3-(4,5-dimethyl-1,2,4-triazol-3-ylthiomethyl)-3-cephem-4-carboxylic acid, 7-(2-thienylsulfinylacetamido)-3-(4-ethyl-1,2,4-triazol-3-ylthiomethyl)-3-cephem-4-carboxylic acid, 7-(2-thienylsulfinylacetamido)-3-(5-ethyl-1,2,4-triazol-3-ylthiomethyl)-3-cephem-4-carboxylic acid, 7-(2-thienylsulfinylacetamido)-3-(1-ethyl-1,2,4-triazol-5-ylthiomethyl)-3-cephem-4-carboxylic acid, 7-(2-thienylsulfinylacetamido)-3-(1-ethyl-1,2,4-triazol-3-ylthiomethyl)-3-cephem-4-carboxylic acid, 7-(2-thienylsulfinylacetamido)-3-(1,5-diethyl-1,2,4-triazol-3-ylthiomethyl)-3-cephem-4-carboxylic acid, 7-(2-thienylsulfinylacetamido)-3-(4,5-diethyl-1,2,4-triazol-3-ylthiomethyl)-3-cephem-4-carboxylic acid, 7-(2-thienylsulfinylacetamido)-3-(1,3-diethyl-1,2,4-triazol-5-ylthiomethyl)-3-cephem-4-carboxylic acid, 7-(2-thienylsulfinylacetamido)-3-(4-methoxymethyl-1,2,4-triazol-3-ylthiomethyl)-3-cephem-4-carboxylic acid, 7-(2-thienylsulfinylacetamido)-3-(4-methyl-5-trifluoromethyl-1,2,4-triazol-3-ylthiomethyl)-3-cephem-4-carboxylic acid, 7-(2-thienylsulfinylacetamido)-3-(4-allyl-1,2,4-triazol-3-ylthiomethyl)-3-cephem-4-carboxylic acid, 7-(2-thienylsulfinylacetamido)-3-(1,2,3-triazol-4-ylthiomethyl)-3-cephem-4-carboxylic acid, 7-(2-thienylsulfinylacetamido)-3-(3-methyl-1,2,3-triazol-4-ylthiomethyl)-3-cephem-4-carboxylic acid, 7-(2-thienylsulfinylacetamido)-3-(5-methyl-1,2,3-triazol-4-ylthiomethyl)-3-cephem-4-carboxylic acid, 7-(2-thienylsulfinylacetamido)-3-(3,5-dimethyl-1,2,3-triazol-4-ylthiomethyl)-3-cephem-4-carboxylic acid, 7-(2-thienylsulfinylacetamido)-3-(3-ethyl-1,2,3-triazol-4-ylthiomethyl)-3-cephem-4-carboxylic acid, 7-(2-thienylsulfinylacetamido)-3-(5-ethyl-1,2,3-triazol-4-ylthiomethyl)-3-cephem-4-carboxylic acid, 7-(2-thienylsulfinylacetamido)-3-(3,5-diethyl-1,2,3-triazol-4-ylthiomethyl)-3-cephem-4-carboxylic acid, 7-(2-thienylsulfinylacetamido)-3-(3-methoxymethyl-1,2,3-triazol-4-ylthiomethyl)-3-cephem-4-carboxylic acid, 7-(2-thienylsulfinylacetamido)-3-(1-ethyl-1H-tetrazol-5-ylthiomethyl)-3-cephem-4-carboxylic acid, 7-(2-thienylsulfinylacetamido)-3-(1H-tetrazol-5-ylthiomethyl)-3-cephem-4-carboxylic acid, 7-(2-thienylsulfinylacetamido)-3-(1-methoxymethyl-1H-tetrazol-5-ylthiomethyl-3-cephem-4-carboxylic acid, 7-(2-thienylsulfinylacetamido)-3-(1,3,4-oxadiazol-2-ylthiomethyl)-3-cephem-4-carboxylic acid, 7-(2-thienylsulfinylacetamido)-3-(5-methyl-1,3,4-oxadiazol-2-ylthiomethyl)-3-cephem-4-carboxylic acid, 7-(2-thienylsulfinylacetamido)-3-(1,3,4-thiadiazol-2-ylthiomethyl)-3-cephem-4-carboxylic acid, 7-(2-thienylsulfinylacetamido)-3-(5-ethyl-1,3,4-thiadiazol-2-ylthiomethyl)-3-cephem-4-carboxylic acid, 7-(2-thienylsulfinylacetamido)-3-(5-trifluoromethyl-1,3,4-thiadiazol-2-ylthiomethyl)-3-cephem-4-carboxylic acid, 7-(2-thienylsulfinylacetamido)-3-(5-n-butyl-1,3,4-thiadiazol-2-ylthiomethyl)-3-cephem-4-carboxylic acid, 7-(2-thienylsulfinylacetamido)-3-(1,2,4-thiadiazol-5-ylthiomethyl)-3-cephem-4-carboxylic acid, 7-(2-thienylsulfinylacetamido)-3-(3-methyl-1,2,4-thiadiazol-5-ylthiomethyl-3-cephem-4-carboxylic acid, 7-(2-thienylsulfinylacetamido)-3-(3-ethyl-1,2,4-thiadiazol-5-ylthiomethyl)-3-cephem-4-carboxylic acid, 7-(2-thienylsulfinylacetamido)-3-(thiazol-5-ylthiomethyl)-3-cephem-4-carboxylic acid, 7-(2-thienylsulfinylacetamido)-3-(2-methylthiazol-5-ylthiomethyl)-3-cephem-4-carboxylic acid, 7-(2-thienylsulfinylacetamido)-3-(4-methylthiazol-5-ylthiomethyl)-3-cephem-4-carboxylic acid, 7-(2-thienylsulfinylacetamido)-3-(2,4-dimethylthiazol-5-ylthiomethyl)-3-cephem-4-carboxylic acid, 7-(2-thienylsulfinylacetamido)-3-(2-ethylthiazol-5-ylthiomethyl)-3-cephem-4-carboxylic acid, 7-(2-thienylsulfinylacetamido)-3-(2,4-diethylthiazol-5-ylthiomethyl)-3-cephem-4-carboxylic acid, 7-(2-thienylsulfinylacetamido)-3-(oxazol-5-ylthiomethyl)-3-cephem-4-carboxylic acid, 7-(2-thienylsulfinylacetamido)-3-(2-methyloxazol-5-ylthiomethyl)-3-cephem-4-carboxylic acid, 7-(2-thienylsulfinylacetamido)-3-(4-methyloxazol-5-ylthiomethyl)-3-cephem-4-carboxylic acid, 7-(2-thienylsulfinylacetamido)-3-(2,4-dimethyloxazol-5-ylthiomethyl)-3-cephem-4-carboxylic acid, 7-(2-thienylsulfinylacetamido)-3-(2-ethyloxazol-5-ylthiomethyl)-3-cephem-4-carboxylic acid, 7-(2-thienylsulfinylacetamido)-3-(2,4-diethyloxazol-5-ylthiomethyl)-3-cephem-4-carboxylic acid, and 7-(2-thienylsulfinylacetamido)-3-(2-pyrazinylthiomethyl)-3-cephem-4-carboxylic acid.

EXAMPLE 6

187 mg of a sodium salt of 7-(2-thienylsulfinylacetamido)cephalosporanic acid of the R form optically active in the sulfoxide, which was obtained according to the method described in Example 1, was dissolved in 1 ml of water, and 780 mg of potassium thiocyanate and 0.05 ml of pyridine were added to the solution. The mixture was heated at 65° to 70° C. for 6 hours, and was then cooled. The resulting solution was diluted with 10 ml of water, and the aqueous solution was passed through a column packed with 13 g of Amberlite XAD-2 (trademark), washed with water and developed with 95% ethanol. The eluate was concentrated to obtain 105 mg of 7-(2-thienylsulfinylacetamido)-3-(1-pyridiniummethyl)-3-cephem-4-carboxylate of the R form optically active in the sulfoxide. The product was excellent in the antimicrobial activity.

EXAMPLE 7

Procedures of Example 1 were repeated by using 7-aminodeacetoxycephalosporanic acid instead of 7-aminocephalosporanic acid to obtain 7-(2-thienylsulfinylacetamido)-3-methyl-3-cephem-4-carboxylic acid of the R form optically active in the sulfoxide. The microbial activity of this product was much superior to that of the product obtained in the same manner by using 2-thienylsulfinylacetic acid having a negative specific rotary power.

EXAMPLE 8

Procedures of Example 1 were repeated by using 7-amino-3-azidomethyl-3-cephem-4-carboxylic acid instead of 7-aminocephalosporanic acid to obtain 7-(2-thienylsulfinylacetamido)-3-azidomethyl-3-caphem-4-carboxylic acid of the R form optically active in the sulfoxide.

EXAMPLE 9

Procedures of Example 1 were repeated by using 7-amino-3-carbamoyloxymethyl-3-cephem-4-carboxylic acid instead of 7-aminocephalosporanic acid to obtain 7-(2-thienylsulfinylacetamido)-3-carbamoyloxymethyl-3-cephem-4-carboxylic acid of the R form optically active in the sulfoxide.

EXAMPLE 10

0.52 g of 4-pyridylsulfinylacetic acid of the R form was dissolved in 20 ml of dry acetone, and 0.5 ml of triethylamine and 2 drops of N,N-dimethylbenzylamine were added to the solution. The solution was agitated and cooled to $-20°$ C., and 0.36 ml of pivaloyl chloride was added dropwise to the solution under agitation. After completion of the dropwise addition, the mixture was agitated at $-20°$ C. for 30 minutes, and at this temperature a mixture of 0.81 g of 7-aminocephalosporanic acid, 0.5 ml of triethylamine and 10 ml of methanol was added at a stroke under violent agitation. Then, the reaction mixture was agitated at $-20°$ C. for 30 minutes, at 0° C. for 1 hour and at room temperature for 2 hours. The reaction mixture was concentrated, and the residue was dissolved in water. The solution was washed with ethyl acetate and with chloroform, and the pH was adjusted to 2.0. The resulting precipitate was removed by filtration, and the filtrate was extracted with chloroform and with ethyl acetate. The ethyl acetate layer was treated with active carbon, dried and concentrated under reduced pressure to obtain 0.27 g of 7-(4-pyridylsulfinylacetamido)cephalosporanic acid of the R form, the IR and NMR spectra of which were found to be in agreement with those of the intended product. The MIC data of the so obtained compound are shown in Table 2.

Table 2

| Bacterium | MIC (μg/ml) of 7-(4-Pyridyl-sulfinylacetamido)cephalasporani Acid (R form) |
|---|---|
| Staphylococcus aureus, ATCC 6538 P | 0.4 |
| Staphylococcus aureus, MS 27 | 1.6 |
| Escherichia coli, NIHJ | 0.8 |
| Escherichia coli, W 3630 | 12.5 |
| Salmonella enteritidis gaertner | 3.2 |
| Klebsiella pneumoniae, ATCC 10031 | 0.8 |
| Shigella sonnei E 33 | 6.3 |
| Proteus vulgaris, OX 19 | 1.6 |
| Proteus rettgeri, ACR | 100 |

EXAMPLE 11

0.52 g of 4-pyridylsulfinylacetic acid of the R form was dissolved in a liquid mixture of 13 ml of dry dimethylsulfoxide and 7 ml of dry acetone, and 0.5 ml of triethylamine and 2 drops of N,N-dimethylbenzylamine were added to the solution. The solution was agitated and cooled to −5° C., and 0.36 ml of pivaloyl chloride was added to the solution under agitation. After completion of the dropwise addition, the mixture was agitated at −5° C. for 20 minutes and at this temperature liquid mixture of 0.64 g of 7-aminodeacetoxycephalosporanic acid, 0.5 ml of triethylamine and 10 ml of methanol was added at a stroke to the above mixture under violent agitation. The reaction mixture was agitated at −5° C. for 30 minutes, at 0° C. for 1 hour and at room temperature for 2 hours. The liquid reaction mixture was concentrated at a temperature lower than 40° C. to distil the reaction solvent, and the residue was dissolved in water. Post treatments were carried out in the same manner as described in Example 10 to obtain 0.12 g of 7-(4-pyridylsulfinylacetamido)-deacetoxycephalosporanic acid of the R form the IR and NMR spectra of which were found to be in agreement with those of the intended product.

EXAMPLE 12

0.57 g of 2-thienylsulfinylacetic acid which was completely of the R form formed by further purifying the 2-thienylsulfinylacetic acid obtained in Referential Example 3 was dissolved in 20 ml of dry acetone, and 0.5 ml of triethylamine and 2 drops of N,N-dimethylbenzylamine were added to the solution. The solution was agitated and cooled to −20° C. Then, 0.36 ml of pivaloyl chloride was added dropwise to the solution under agitation, and the mixture was agitated at −20° C. for 30 minutes. At this temperature, a liquid mixture of 0.81 g of 7-aminocephalosporanic acid, 0.5 ml of triethylamine and 10 ml of methanol was added at a stroke to the above mixture under violent agitation. The reaction mixture was agitated at −20° C. for 30 minutes, at 0° C. for 1 hour and at room temperature for 2 hours. In the same manner as described in Example 1, the reaction mixture was post-treated to obtain 0.31 g of 7-(2-thienylsulfinylacetamido)cephalosporanic acid of the R form, the IR and NMR spectra of which were found to be in agreement with the intended product.

EXAMPLE 13

Procedures of Example 10 were repeated by using 3-thienylsulfinylacetic acid of the R form instead of the 4-pyridylsulfinylacetic acid, and the resulting reaction mixture was post-treated in the same manner as in Example 1 to obtain 7-(3-thienylsulfinylacetamido)-cephalosporanic acid of the R form.

EXAMPLE 14

Procedures of Example 10 were repeated by using 5-methyl-1,3,4-thiadiazol-2-ylsulfinylacetic acid of the R form instead of the 2-pyridylsulfinylacid, and the reaction mixture was post-treated in the same manner as in Example 1 to obtain 7-(5-methyl-1,3,4-thiadiazol-2-ylsulfinylacetamido)cephalosporanic acid of the R form.

EXAMPLE 15

Procedures of Example 11 were repeated by using 1-methyl-1H-tetrazol-5-ylsulfinylacetic acid of the R form instead of the 4-pyridylsulfinylacetic acid to obtain 7-(1-methyl-1H-tetrazol-5-ylsulfinylacetamido)-deacetoxycephalosporanic acid of the R form.

EXAMPLE 16

0.46 g of a sodium salt of 7-(2-pyridylsulfinylacetamido)cephalosporanic acid of the R form obtained according to the method described in Example 10 using 2-pyridylsulfinylacetic acid was dissolved in 1 ml of water, and 1.97 g of potassium thiocyanate, 0.5 ml of water and 0.11 ml of pyridine were added to the solution. The mixture was heated at 65° to 70° C. for 6 hours, and then, it was cooled. The resulting solution was diluted with 20 ml of water, and the solution was passed through a column packed with 40 g of Amberlite XAD-2 (trademark), washed with water and developed with 95% ethanol. The eluate was collected and concentrated to obtain 0127 g of 7-(2-pyridylsulfinylacetamido)-3-(1-pyridiniummethyl)-3-cephem-4-carboxylate of the R form, the IR and NMR spectra of which were found to be in agreement with those of the intended product.

EXAMPLE 17

Procedures of Example 10 were repeated by using 2-pyridylsulfinylacetic acid and 7-amino-3-(2-methyl-1,3,4-thiadiazol-5-ylthiomethyl)-3-cephem-4-carboxylic acid instead of the 4-pyridylsulfinylacetic acid and the 7-aminocephalosporanic acid respectively to obtain 7-(2-pyridylsulfinylacetamido)-3-(2-methyl-1,3,4-thiadiazol-5-ylthiomethyl)-3-cephem-4-carboxylic acid of the R form.

EXAMPLE 18

Procedures of Example 10 were repeated by using a 3-4-lactone of 7-amino-3-hydroxymethyl-3-cephem-4-carboxylic acid instead of the 7-aminocephalosporanic acid to obtain a 3-4-lactone of 7-(2-pyridylsulfinylacetamido)-3-hydroxymethyl-3-cephem-4-carboxylic acid of the R form.

EXAMPLE 19

0.34 g of phenylsulfinylacetic acid of the R form ($[\alpha]_D^{20}$: +183°, C=1.00, ethanol) was dissolved in 8 ml of dry acetone, and 0.28 ml of triethylamine and 1 drop of N,N-dimethylbenzylamine were added to the solution. The solution was agitated and cooled to −20° C., and 0.24 g of pivaloyl chloride was added to the solution under agitation. The solution was agitated at −20° C. for 30 minutes and at this temperature, a liquid mixture of 0.54 g of 7-aminocephalosporanic acid, 0.28 ml of triethylamine and 4 ml of methanol was added at a stroke to the above solution under violent agitation. Then, the mixture was agitated at −20° C. for 30 minutes, at 0° C. for 1 hour and at room temperature for 2 hours. Then, the solvent was distilled under reduced pressure and the residue was dissolved in water. The solution was washed with ethyl acetate, and the pH of the aqueous layer was adjusted to 2.5 by 2 N hydrochloric acid and the aqueous layer was extracted with a small quantity of chloroform and then with ethyl acetate. The ethyl acetate layer was dried and concentrated under reduced pressure to obtain 0.18 g of 7-(phenylsulfinylacetamido)cephalosporanic acid of the R form, the IR and NMR spectra of which were found to be in agreement with those of the intended product.

The minimum inhibitory concentrations (MIC) of the so obtained compound to various Gram-positive bacteria and Gram-negative bacteria are shown in Table 3. For comparison, MIC data of the comparative product synthesized similarly by using phenylsulfinylacetic acid having a specific rotation $[\alpha]_D^{20}$ of −182° are also shown in Table 3. The specific rotation $[\alpha]_D^{20}$ was measured in ethanol at a concentration of 1.00%.

Table 3

| Bacterium | 7-(Phenylsulfinyl-acetamido)cephalo-sporanic acid | 7-(Phenylsulfinyl-acetamido)cephalo-sporanic acid |
|---|---|---|
| $[\alpha]_D^{20}$ of starting phenylsulfinyl-acetic acid | +183° | −182° |
| Staphylococcus aureus, 6538 P | 0.2 | 25 |
| Staphylococcus aureus, MS 27 | 0.8 | 50 |
| Escherichia coli, NIHJ | 1.6 | 100 |
| Escherichia coli, W 3630 | 12.5 | 100 |
| Escherichia coli, PS 3 | 6.3 | 100 |
| Escherichia coli, RGN 14 | 12.5 | 100 |
| Escherichia coli, RGN 238 | 12.5 | 100 |
| Salmonella enteritidis gaertner | 3.2 | 50 |
| Enterobacter 0655 | 100 | 100 |
| Shigella sonnei E 33 | 6.3 | 100 |
| Proteus vulgaris, OX 19 | 1.6 | 100 |
| Proteus rettgeri, ACR | 100 | 100 |
| Pseudomonas aeruginosa, IAM 1095 | 100 | 100 |
| Klebsiella pneumoniae, ATCC 10031 | 1.6 | 50 |

EXAMPLE 20

0.37 g of phenylsulfinylacetic acid of the R form containing minute amounts of impurities ($[\alpha]_D^{20}$: +134, C=1.00, ethanol) was dissolved in 8 ml of dry acetone, and 0.28 ml of triethylamine and 1 drop of N,N-dimethylbenzylamine were added to the solution. The solution was agitated and cooled to −20° C. Then, 0.24 g of isovaleryl chloride was added to the solution under agitation, and the solution was added at −20° C. for 30 minutes. Then, a liquid mixture of 0.43 g of 7-aminodeacetoxycephalosporanic acid, 0.28 ml of triethylamine and 4 ml of methanol was added at a stroke to the above solution at the above temperature under violent agitation. Then, the mixture was agitated at −20° C. for 30 minutes, at 0° C. for 1 hour and at room temperature for 2 hours to effect reaction. The reaction mixture was post-treated in the same manner as described in Example 19 to obtain 0.21 g of 7-(phenylsulfinylacetamido)deacetoxycephalosporanic acid of the R form, the IR and NMR spectra of which were found to be in agreement with those of the intended product.

EXAMPLE 21

To 8 ml of methylene chloride were added 0.37 g of phenylsulfinylacetic acid of the R form ($[\alpha]_D^{20}$: +183°, C=1.00, ethanol) and 0.41 g of dicyclohexylcarbodiimide, and the mixture was agitated at room temperature for 1.5 hours. Then, a solution consisting of 0.69 g of 7-amino-3-(2-methyl-1,3,4-thiadiazol-5-ylthiomethyl)-3-cephem-4-carboxylic acid, 0.28 ml of triethylamine and 8 ml of methylene chloride was added to the above mixture, and the resulting mixture was agitated at room temperature overnight. The reaction mixture was filtered, and the filtrate was post-treated in the same manner as described in Example 19 to obtain 0.17 g of 7-(phenylsulfinylacetamido)-3-(2-methyl-1,3,4-thiadiazol-5-ylthiomethyl)-3-cephem-4-carboxylic acid of the R form, the IR and NMR spectra of which were found to be in agreement with those of the intended product.

EXAMPLE 22

184 mg of a sodium salt of 7-(phenylsulfinylacetamido)cephalosporanic acid of the R form obtained in the same manner as described in Example 20 by using phenylsulfinylacetic acid of the R form having a specific rotation $[\alpha]_D^{29}$ of +134° (C=1.00, ethanol), was dissolved in 1 ml of water, and 780 mg of potassium thiocyanate and 0.05 ml of pyridine were added to the solution. Then, the mixture was heated at 65° to 70° C. for 6 hours and then cooled. The resulting solution was diluted with 10 ml of water, passed through a column packed with 13 g of Amberlite XAD-2 (trademark), washed with water and developed with 95% ethanol. The eluate was concentrated to obtain 110 mg of 7-(phenylsulfinylacetamido)-3-(1-pyridiniummethyl)-3-cephem-4-carboxylate of the R form, the IR and NMR spectra of which were found to be in agreement with those of the intended product.

EXAMPLE 23

Procedures of Example 19 were repeated by using 7-amino-3-(tetrazol-5-ylthiomethyl)-3-cephem-4-carboxylic acid instead of the 7-aminocephalosporanic acid to obtain 7-(phenylsulfinylacetamido)-3-(tetrazol-5-ylthiomethyl)-3-cephem-4-carboxylic acid of the R form.

EXAMPLE 24

Procedures of Example 19 were repeated by using a 3-4-lactone of 7-amino-3-hydroxymethyl-3-cephem-4-carboxylic acid instead of the 7-aminocephalosporanic acid to obtain a 3-4-lactone of 7-(phenylsulfinylacetamido)-3-hydroxymethyl-3-cephem-4-carboxylic acid of the R form.

What is claimed is:
1. A cephalosporin represented by the following formula, in which the sulfinyl group is of the R form:

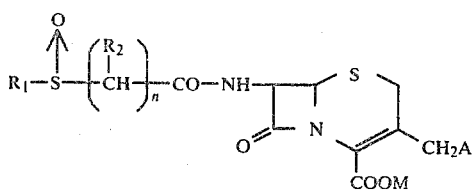

wherein
R₁ stands for
(1) a heterocyclic group which is selected from the group consisting of a thienyl group, a furyl group, a pyridyl group, a thiadiazolyl group, and a tetrazolzyl group,
(2) a substituted thiadiazolyl group, triazolyl group, or pyridyl group, wherein the substituent is selected from the group consisting of lower alkyl wherein the lower alkyl is selected from the group consisting of methyl, ethyl, propyl, isopropyl, butyl, isobutyl and amyl, allyl, trifluoromethyl, and lower alkoxymethyl or
(3) a substituted thienyl or furyl group wherein the substituent is selected from the group consisting of lower alkyl as defined above, allyl and lower alkoxymethyl;

R₂ stands for a hydrogen atom or a lower alkyl group as defined above;

A stands for a hydrogen atom, azido, lower alkoxy a lower alkanoyloxy group, wherein the lower alkyl group thereof is as defined above, a pyridinium group an N,N'-dibenzylpyridinium group, a quinolinium group, a picolinium group, a carbamoyloxy group, a lower alkyl mercapto group, wherein the lower alkyl group is as defined above, a heterocyclic-mercapto group wherein the heterocyclic group is selected from the group consisting of a thienyl group, a furyl group, a pyridyl group, a imidazolyl group, an oxazolyl group, oxadiazolyl groups, a thiazolyl group, thiadiazolyl groups, triazolyl groups, a pyrimidyl group, a tetrazolyl group, a benzothiazolyl group, a isoxazolyl group, a benzoxazolyl group, a benzoimidazolyl group, a benzoxazinyl group, a benzothiazinyl group, a pyridazinyl group, an N-oxopyridyl group, an N-oxopyridazinyl group and an oxopyrimidyl group, a substituted heterocyclic-mercapto group, wherein the heterocyclic group is as defined above for heterocyclic-mercapto or an oxopyrimidyl group, and the substituent when the heterocyclic group contains nitrogen is lower alkyl as defined above, allyl, trifluoromethyl or lower alkoxymethyl, and the substituent when the heterocyclic group does not contain nitrogen is lower alkyl as defined above, allyl or lower alkoxymethyl as defined above;

M stands for a hydrogen atom, a lower alkyl group as defined above, a benzyl group, a bromobenzyl group, a methoxybenzyl group, a phenethyl group, a chlorophenethyl group, a diethylbenzyl group, a trichlorobenzyl group, a group —CH₂OCOR₃ in which R₃ is a lower alkyl group as defined above, a phenyl group, a substituted phenyl group having 1 to 3 substituents which are selected from the group consisting of halogen atoms, lower alkyl groups, wherein the lower alkyl is selected from the group consisting of methyl, ethyl, propyl, isopropyl, butyl, isobutyl and amyl groups, lower alkoxy groups wherein the lower alkyl portion thereof is as defined above, hydroxy groups, cyano groups, carboxy groups, amino groups, and di-(lower alkylamino groups wherein the lower alkyl group is as defined above, a naphthyl group, a benzyl group, a bromobenzyl group, a methoxybenzyl group, a phenethyl group, a chlorophenethyl group, a diethylbenzyl group or a trichlorobenzyl group, a phenacyl group, a pharmacologically acceptable non-toxic cation, an anionic charge, or a monovalent carbon-oxygen bond when taken together with A; and n is 1, 2 or 3, wherein said R form is defined to indicate an optical isomer having steroechemically the same structure as that of an optical isomer having a positive specific rotation [α]$_D$ in ethanol between two sulfinyl group stereoisomers of a compound represented by the following formula:

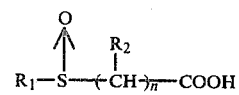

wherein R₁, R₂ and n are as defined above.

2. A cephalosporin as set forth in claim 1 wherein A stands for a hydrogen atom, a lower alkanoyloxy group, a pyridinium group, a carbamoyloxy group a methoxy group, a methylthio group, a heterocyclic-mercapto group, wherein the heterocyclic group is selected from the group consisting of thienyl, pyridyl, N-oxopyridyl, imidazolyl, oxazolyl, oxadiazolyl, thiazolyl, thiadiazolyl, triazolyl, pyrimidyl, oxopyrimidyl, tetrazolyl, pyridazinyl and N-oxopyridazinyl, a substituted heterocyclicmercapto group, wherein the heterocyclic group is selected from the group consisting of thienyl, pyridyl, N-oxopyridyl, imidazolyl, oxazolyl, oxadiazolyl, thiazolyl, thiadiazolyl, triazolyl, pyrimidyl, oxopyrimidyl, tetrazolyl, pyridazinyl and N-oxopyridazinyl, and the substituent is selected from the group consisting of methyl, ethyl, n-butyl, methoxymethyl, allyl, and trifluoromethyl, an azido group, or a monovalent carbon-oxygen bond in the lactone ring when taken together with M.

3. A cephalosporin as set forth in claim 1 wherein M stands for a hydrogen atom, a pharmacologically acceptable non-toxic cation, or a monovalent carbon-oxygen bond when taken together with A.

4. A cephalosporin as set forth in claim 1 wherein R₁ stand for
(1) a heterocyclic group which is selected from the group consisting of thienyl, pyridyl, thiadiazolyl, tetrazolyl, and furyl, or
(2) a substituted heterocyclic group wherein the heterocyclic group is as defined above and the substituent is selected from the group consisting of methyl, ethyl and n-propyl.

5. A cephalosporin as set forth in claim 4 wherein A is a hydrogen atom, a lower alkanoyloxy group, a pyridinium group, a carbamoyloxy group, a methoxy group, a heterocyclic-mercapto group, wherein the heterocyclic group is selected from the group consisting of thienyl, pyridyl, N-oxopyridyl, imidazolyl, oxazolyl, oxadiazolyl, thiazolyl, thiadiazolyl, triazolyl, pyrimidyl, oxopyrimidyl, tetrazolyl, pyridazinyl and N-oxopyridazinyl, a substituted heterocyclic-mercapto group, wherein the heterocyclic group is selected from the group consisting of thienyl, pyridyl, N-oxopyridyl, imidazolyl, oxazolyl, oxadiazolyl, thiazolyl, thiadiazolyl, triazolyl, pyrimidyl, oxopyrimidyl, tetrazolyl, pyridazinyl and N-oxopyridazinyl, and the substituent is selected from the group consisting of methyl, ethyl, n-butyl, methoxymethyl, allyl, trifluoromethyl an azido group, or a monovalent carbon-oxygen bond in the lactone ring when taken together with M.

6. A cephalosporin as set forth in claim 5 wherein M stands for a hydrogen atom, a pharmacologically acceptable non-toxic cation or a monovalent carbon-oxygen bond when taken together with A.

7. A cephalosporin as set forth in claim 6 wherein $R_1$ is selected from the group consisting of 2-thienyl, 3-thienyl, 4-pyridyl, 2-pyridyl, 1,3,4-thiadiazol-2-yl, 5-methyl-1,3,4-thiadiazol-2-yl, and 1-methyl-1H-tetrazol-5-yl.

8. A cephalosporin as set forth in claim 7 wherein A is selected from the group consisting of a hydrogen atom, acetoxy, pyridinium, carbamoyloxy, azido, 2-thienylthio, 2-pyridylthio, 4-N-oxopyridylthio, 1,3-pyrimidyl-4-thio, 1,3-pyrimidyl-2-thio, 1,3,4-oxadiazol-2-ylthio, 5-methyl-1,3,4-oxadiazol-2-ylthio, 1,3-oxazol-5-ylthio, 2-methyl-1,3-oxazol-5-ylthio, 4-methyl-1,3-oxazol-5-ylthio, 2-ethyl-1,3-oxazol-5-ylthio, 2,4-dimethyl-1,3-oxazol-5-ylthio, 2,4-diethyl-1,3-oxazol-5-ylthio, 1,3,4-thiadiazol-2-ylthio, 5-methyl-1,3,4-thiadiazol-2-ylthio, 5-ethyl-1,3,4-thiadiazol-2-ylthio, 5-n-butyl-1,3,4-thiadiazol-2-ylthio, 5-trifluoromethyl-1,3,4-thiadiazol-2-ylthio, 1,2,4-thiadiazol-5-ylthio, 3-methyl-1,2,4-thiadiazol-5-ylthio, 3-ethyl-1,2,4-thiadiazol-5-ylthio, 5-methyl-1,3,4-triazol-2-ylthio, 1-methyl-1,3,4-triazol-2-ylthio, 1H-1,4,5-triazol-2-ylthio, 1-methyl-1,4,5-triazol-2-ylthio, 1-ethyl-1,4,5-triazol-2-ylthio, 3-methyl-1,4,5-triazol-2-ylthio, 1,3-dimethyl-1,4,5-triazol-2-ylthio, 1,3-diethyl-1,4,5-triazol-2-ylthio, 1-methyl-1,3,5-triazol-2-ylthio, 1,4-dimethyl-1,3,5-triazol-2-ylthio, 1,4-diethyl-1,3,5-triazol-2-ylthio, 1,2,3,4-tetrazol-2-ylthio, 1-methyl-1H-tetrazol-5-ylthio, 1-methoxymethyl-1H-tetrazol-5-ylthio, 1,2-pyridazin-2-ylthio, 1-N-oxo-1,2-pyridazin-2-ylthio, 2-N-oxo-1,2-pyridazin-2-ylthio, 1,5-pyrimidyl-2-thio, 1,3-pyrimidyl-2-thio, 2-oxo-4-pyrimidylthio and 2-oxo-5-methyl-4-pyrimidylthio.

9. A cephalosporin as set forth in claim 8 wherein A is a hydrogen atom, acetoxy, 1-methyl-1H-tetrazol-5-ylthio or 5-methyl-1,3,4-thiadiazol-2-ylthio.

10. A cephalosporin as set forth in claim 6 wherein $R_1$ is selected from the group consisting of 2-thienyl, 3-thienyl, 2-pyridyl, 4-pyridyl, 5-methyl-1,3,4-thiadiazol-2-yl, 1,3,4-thiadiazol-2-yl and 1 methyl-1-H-tetrazol-5-yl.

11. A cephalosporin as set forth in claim 10 wherein M is selected from the group consisting of a hydrogen atom, an alkali metal, an amine salt ion and an anionic charge.

12. A cephalosporin as set forth in claim 11 wherein n is 1, and $R_2$ is a hydrogen atom.

13. A cephalosporin as set forth in claim 12 wherein M is selected from the group consisting of a hydrogen atom and a sodium atom.

14. A compound according to claim 1 which is 7-(2-thienylsulfinylacetamido)cephalosporanic acid of the R form.

15. A compound according to claim 1 which is 7-(2-thienylsulfinylacetamido)-3-(5-methyl-1,3,4-thiadiazol-2-ylthiomethyl)-3-cephem-4-carboxylic acid of the R form.

16. A compound according to claim 1 which is sodium 7-(2-thienylsulfinylacetamido)-3-(1-methyl-1H-tetrazol-5-ylthiomethyl)-3-cephem-4-carboxylate of the R form.

17. A compound according to claim 1 which is 7-(2-thienylsulfinylacetamido)-3-(2-pyridylthiomethyl)-3-cephem-4-carboxylic acid of the R form or its sodium salt.

18. A compound according to claim 1 which is 7-(2-thienylsulfinylacetamido)-3-(4-pyridylthiomethyl)-3-cephem-4-carboxylic acid of the R form or its sodium salt.

19. A compound according to claim 1 which is 7-(2-thienylsulfinylacetamido)-3-(1-oxo-4-pyridylthiomethyl)-3-cephem-4-carboxylic acid of the R form or its sodium salt.

20. A compound according to claim 1 which is 7-(2-thienylsulfinylacetamido)-3-(4-pyrimidylthiomethyl)-3-cephem-4-carboxylic acid of the R form or its sodium salt.

21. A compound according to claim 1 which is 7-(2-thienylsulfinylacetamido)-3-(2-oxo-4-pyrimidylthiomethyl)-3-cephem-4-carboxylic acid of the R form or its sodium salt.

22. A compound according to claim 1 which is 7-(2-thienylsulfinylacetamido)-3-(2-oxo-5-methyl-4-pyrimidylthiomethyl)-3-cephem-4-carboxylic acid of the R form or its sodium salt.

23. A compound according to claim 1 which is 7-(2-thienylsulfinylacetamido)-3-(3-pyridazinylthiomethyl)-3-cephem-4-carboxylic acid of the R form or its sodium salt.

24. A compound according to claim 1 which is 7-(2-thienylsulfinylacetamido)-3-(1-oxo-3-pyridazinylthiomethyl)-3-cephem-4-carboxylic acid of the R form or its sodium salt.

25. A compound according to claim 1 which is 7-(2-thienylsulfinylacetamido)-3-(2-oxo-3-pyridazinylthiomethyl)-3-cephem-4-carboxylic acid of the R form or its sodium salt.

26. A compound according to claim 1 which is 7-(2-thienylsulfinylacetamido)-3-(2-thienylthiomethyl)-3-cephem-4-carboxylic acid of the R form or its sodium salt.

27. A compound according to claim 1 which is 7-(2-thienylsulfinylacetamido)-3-(4-methyl-1,2,4-triazol-3-ylthiomethyl)-3-cephem-4-carboxylic acid of the R form or its sodium salt.

28. A compound according to claim 1 which is 7-(2-thienylsulfinylacetamido)-3-(5-methyl-1,2,4-triazol-3-ylthiomethyl)-3-cephem-4-carboxylic acid of the R form or its sodium salt.

29. A compound according to claim 1 which is 7-(2-thienylsulfinylacetamido)-3-(1-methyl-1,2,4-triazol-5-ylthiomethyl)-3-cephem-5-carboxylic acid of the R form or its sodium salt.

30. A compound according to claim 1 which is 7-(2-thienylsulfinylacetamido)-3-(1-methyl-1,2,4-triazol-3-ylthiomethyl)-3-cephem-4-carboxylic acid of the R form or its sodium salt.

31. A compound according to claim 1 which is 7-(2-thienylsulfinylacetamido)-3-(1,5-dimethyl-1,2,4-triazol-3-ylthiomethyl)-3-cephem-4-carboxylic acid of the R form or its sodium salt.

32. A compound according to claim 1 which is 7-(2-thienylsulfinylacetamido)-3-(1,3-dimethyl-1,2,4-triazol-5-ylthiomethyl)-3-cephem-4-carboxylic acid of the R form or its sodium salt.

33. A compound according to claim 1 which is 7-(2-thienylsulfinylacetamido)-3-(4,5-dimethyl-1,2,4-triazol-3-ylthiomethyl)-3-cephem-4-carboxylic acid of the R form or its sodium salt.

34. A compound according to claim 1 which is 7-(2-thienylsulfinylacetamido)-3-(4-ethyl-1,2,4-triazol-3-ylthiomethyl)-3-cephem-4-carboxylic acid of the R form or its sodium salt.

35. A compound according to claim 1 which is 7-(2-thienylsulfinylacetamido)-3-(5-ethyl-1,2,4-triazol-3-ylthiomethyl)-3-cephem-4-carboxylic acid of the R form or its sodium salt.

36. A compound according to claim 1 which is 7-(2-thienylsulfinylacetamido)-3-(1-ethyl-1,2,4-triazol-5-ylthiomethyl)-3-cephem-4-carboxylic acid of the R form or its sodium salt.

37. A compound according to claim 1 which is 7-(2-thienylsulfinylacetamido)-3-(1-ethyl-1,2,4-triazol-3-ylthiomethyl)-3-cephem-4-carboxylic acid of the R form or its sodium salt.

38. A compound according to claim 1 which is 7-(2-thienylsulfinylacetamido)-3-(1,5-diethyl-1,2,4-triazol-3-ylthiomethyl)-3-cephem-4-carboxylic acid of the R form or its sodium salt.

39. A compound according to claim 1 which is 7-(2-thienylsulfinylacetamido)-3-(4,5-diethyl-1,2,4-triazol-3-ylthiomethyl)-3-cephem-4-carboxylic acid of the R form or its sodium salt.

40. A compound according to claim 1 which is 7-(2-thienylsulfinylacetamido)-3-(1,3-diethyl-1,2,4-triazol-5-ylthiomethyl)-3-cephem-4-carboxylic acid of the R form or its sodium salt.

41. A compound according to claim 1 which is 7-(2-thienylsulfinylacetamido)-3-(4-methoxymethyl-1,2,4-triazol-3-ylthiomethyl)-3-cephem-4-carboxylic acid of the R form or its sodium salt.

42. A compound according to claim 1 which is 7-(2-thienylsulfinylacetamido)-3-(4-methyl-5-trifluoromethyl-1,2,4-triazol-3-ylthiomethyl)-3-cephem-4-carboxylic acid of the R form or its sodium salt.

43. A compound according to claim 1 which is 7-(2-thienylsulfinylacetamido)-3-(4-allyl-1,2,4-triazol-3-ylthiomethyl)-3-cephem-4-carboxylic acid of the R form or its sodium salt.

44. A compound according to claim 1 which is 7-(2-thienylsulfinylacetamido)-3-(1,2,3-triazol-4-ylthiomethyl)-3-cephem-4-carboxylic acid of the R form or its sodium salt.

45. A compound according to claim 1 which is 7-(2-thienylsulfinylacetamido)-3-(2-methyl-1,2,3-triazol-4-ylthiomethyl)-3-cephem-4-carboxylic acid of the R form or its sodium salt.

46. A compound according to claim 1 which is 7-(2-thienylsulfinylacetamido)-3-(5-methyl-1,2,3-triazol-4-ylthiomethyl)-3-cephem-4-carboxylic acid of the R form or its sodium salt.

47. A compound according to claim 1 which is 7-(2-thienylsulfinylacetamido)-3-(3,5-dimethyl-1,2,3-triazol-4-ylthiomethyl)-3-cephem-4-carboxylic acid of the R form or its sodium salt.

48. A compound according to claim 1 which is 7-(2-thienylsulfinylacetamido)-3-(3-ethyl-1,2,3-triazol-4-ylthiomethyl)-3-cephem-4-carboxylic acid of the R form or its sodium salt.

49. A compound according to claim 1 which is 7-(2-thienylsulfinylacetamido)-3-(5-ethyl-1,2,3-triazol-4-ylthiomethyl)-3-cephem-4-carboxylic acid of the R form or its sodium salt.

50. A compound according to claim 1 which is 7-(2-thienylsulfinylacetamido)3-(3,5-diethyl-1,2,3-triazol-4-ylthiomethyl)-3-cephem-4-carboxylic acid of the R form or its sodium salt.

51. A compound according to claim 1 which is 7-(2-thienylsulfinylacetamido)-3-(3-methoxymethyl-1,2,3-triazol-4-ylthiomethyl)-3-cephem-4-carboxylic acid of the R form or its sodium salt.

52. A compound according to claim 1 which is 7-(2-thienylsulfinylacetamido)-3-(1-ethyl-1H-tetrazol-5-ylthiomethyl)-3-cephem-4-carboxylic acid of the R form or its sodium salt.

53. A compound according to claim 1 which is 7-(2-thienylsulfinylacetamido)-3-(1H-tetrazol-5-ylthiomethyl)-3-cephem-4-carboxylic acid of the R form or its sodium salt.

54. A compound according to claim 1 which is 7-(2-thienylsulfinylacetamido)-3-(1-methoxymethyl-1H-tetrazol-5-ylthiomethyl-3-cephem-4-carboxylic acid of the R form or its sodium salt.

55. A compound according to claim 1 which is 7-(2-thienylsulfinylacetamido)-3-(1,3,4-oxadiazol-2-ylthiomethyl)-3-cephem-4-carboxylic acid of the R form or its sodium salt.

56. A compound according to claim 1 which is 7-(2-thienylsulfinylacetamido)-3-(5-methyl-1,3,4-oxadiazol-2-ylthiomethyl)-3-cephem-4-carboxylic acid of the R form or its sodium salt.

57. A compound according to claim 1 which is 7-(2-thienylsulfinylacetamido)-3-(1,3,4-thiadiazol-2-ylthiomethyl)-3-cephem-4-carboxylic acid of the R form or its sodium salt.

58. A compound according to claim 1 which is 7-(2-thienylsulfinylacetamido)-3-(5-ethyl-1,3,4-thiadiazol-2-ylthiomethyl)-3-cephem-4-carboxylic acid of the R form or its sodium salt.

59. A compound according to claim 1 which is 7-(2-thienylsulfinylacetamido)-3-(5-trifluoromethyl-1,3,4-thiadiazol-2-ylthiomethyl)-3-cephem-4-carboxylic acid of the R form or its sodium salt.

60. A compound according to claim 1 which is 7-(2-thienylsulfinylacetamido)-3-(5-n-butyl-1,3,4-thiadiazol-2-ylthiomethyl)-3-cephem-4-carboxylic acid of the R form or its sodium salt.

61. A compound according to claim 1 which is 7-(2-thienylsulfinylacetamido)-3-(1,2,4-thiadiazol-5-ylthiomethyl)-3-cephem-4-carboxylic acid of the R form or its sodium salt.

62. A compound according to claim 1 which is 7-(2-thienylsulfinylacetamido)-3-(3-methyl-1,2,4-thiadiazol-5-ylthiomethyl)-3-cephem-4-carboxylic acid of the R form or its sodium salt.

63. A compound according to claim 1 which is 7-(2-thienylsulfinylacetamido)-3-(3-ethyl-1,2,4-thiadiazol-5-ylthiomethyl)-3-cephem-4-carboxylic acid of the R form or its sodium salt.

64. A compound according to claim 1 which is 7-(2-thienylsulfinylacetamido)-3-(thiazol-5-ylthiomethyl)-3-cephem-4-carboxylic acid of the R form or its sodium salt.

65. A compound according to claim 1 which is 7-(2-thienylsulfinylacetamido)-3-(2-methylthiazol-5-ylthiomethyl)-3-cephem-4-carboxylic acid of the R form or its sodium salt.

66. A compound according to claim 1 which is 7-(2-thienylsulfinylacetamido)-3-(4-methylthiazol-5-ylthiomethyl)-3-cephem-4-carboxylic acid of the R form or its sodium salt.

67. A compound according to claim 1 which is 7-(2-thienylsulfinylacetamido)-3-(2,4-dimethylthiazol-5-ylthiomethyl-3-cephem-4-carboxylic acid of the R form or its sodium salt.

68. A compound according to claim 1 which is 7-(2-thienylsulfinylacetamido)-3-(2-ethylthiazol-5-ylthiomethyl)-3-cephem-4-carboxylic acid of the R form or its sodium salt.

69. A compound according to claim 1 which is 7-(2-thienylsulfinylacetamido)-3-(2,4-diethylthiazol-5-ylthiomethyl)-3-cephem-4-carboxylic acid of the R form or its sodium salt.

70. A compound according to claim 1 which is 7-(2-thienylsulfinylacetamido)-3-(oxazol-5-ylthiomethyl)-3-cephem-4-carboxylic acid of the R form or its sodium salt.

71. A compound according to claim 1 which is 7-(2-thienylsulfinylacetamido)-3-(2-methyloxazol-5-ylthiomethyl)-3-cephem-4-carboxylic acid of the R form or its sodium salt.

72. A compound according to claim 1 which is 7-(2-thienylsulfinylacetamido)-3-(4-methyloxazol-5-ylthiomethyl)-3-cephem-4-carboxylic acid of the R form or its sodium salt.

73. A compound according to claim 1 which is 7-(2-thienylsulfinylacetamido)-3-(2,4-dimethyloxazol-5-ylthiomethyl)-3-cephem-4-carboxylic acid of the R form or its sodium salt.

74. A compound according to claim 1 which is 7-(2-thienylsulfinylacetamido)-3-(2-ethyloxazol-5-ylthiomethyl)-3-cephem-4-carboxylic acid of the R form or its sodium salt.

75. A compound according to claim 1 which is 7-(2-thienylsulfinylacetamido)-3-(2,4-diethyloxazol-5-ylthiomethyl)-3-cephem-4-carboxylic acid of the R form or its sodium salt.

76. A compound according to claim 1 which is 7-(2-thienylsulfinylacetamido)-3-(1-pyridiniummethyl)-3-cephem-4-carboxylate of the R form.

77. A compound according to claim 1 which is 7-(2-thienylsulfinylacetamdio)-3-methyl-3-cephem-4-carboxylic acid of the R form.

78. A compound according to claim 1 which is 7-(2-thienylsulfinylacetamido)-3-azidomethyl-3-cephem-4-carboxylic acid of the R form.

79. A compound according to claim 1 which is 7-(2-thienylsulfinylacetamido)-3-carbamoyloxymethyl-3-cephem-4-carboxylic acid of the R form.

80. A compound according to claim 1 which is 7-(4-pyridylsulfinylacetamido)cephalosporanic acid of the R form.

81. A compound according to claim 1 which is 7-(4-pyridylsulfinylacetamido)deacetoxycephalosporanic acid of the R form.

82. A compound according to claim 1 which is 7-(3-thienylsulfinylacetamido)cephalosporanic acid of the R form.

83. A compound according to claim 1 which is 7-(5-methyl-1,3,4-thiadiazol-2-ylsulfinylacetamido)cephalosporanic acid of the R form.

84. A compound according to claim 1 which is 7-(1-methyl-1H-tetrazol-5-ylsulfinylacetamido)deacetoxycephalosporanic acid of the R form.

85. A compound according to claim 1 which is 7-(2-pyridylsulfinylacetamido)-3-(1-pyridiniummethyl)-3-cephem-4-carboxylate of the R form.

86. A compound according to claim 1 which is 7-(2-pyridylsulfinylacetamido)-3-(2-methyl-1,3,4-thiadiazol-5-ylthiomethyl)-3-cephem-4-carboxylic acid of the R form.

* * * * *